(12) United States Patent
Esnouf

(10) Patent No.: US 6,508,250 B1
(45) Date of Patent: *Jan. 21, 2003

(54) DISPOSABLE OXYGENATING DEVICE

(76) Inventor: Philip Stuart Esnouf, 4 Balfour Street, Toorak, Victoria 3142 (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/534,646

(22) Filed: Mar. 23, 2000

Related U.S. Application Data

(63) Continuation of application No. 09/043,234, filed as application No. PCT/AU96/00417 on Sep. 12, 1995, now Pat. No. 6,098,621.

(30) Foreign Application Priority Data

Sep. 12, 1995 (AU) .............................................. PN5384

(51) Int. Cl.[7] ............................................. A61M 16/00
(52) U.S. Cl. .......................... 128/205.13; 128/203.28; 128/205.14; 128/205.17
(58) Field of Search ...................... 128/203.28, 204.26, 128/204.28, 205.13–205.15, 205.17, 205.24, 914

(56) References Cited

U.S. PATENT DOCUMENTS

| | | | |
|---|---|---|---|
| 2,208,633 A | 7/1940 | Heidbrink | |
| 2,535,938 A | 12/1950 | Lombard | |
| 2,818,861 A | * 1/1958 | Russell | 128/205.24 |
| 3,196,866 A | * 7/1965 | Adams | 128/205.13 |
| 3,796,216 A | 3/1974 | Schwarz | |
| 3,890,967 A | * 6/1975 | Elam et al. | 128/201.25 |
| 3,960,148 A | 6/1976 | Dryden | |
| 4,029,093 A | 6/1977 | Køhnke | |
| 4,077,404 A | 3/1978 | Elam | |
| 4,088,131 A | * 5/1978 | Elam et al. | 128/204.28 |
| 4,119,097 A | * 10/1978 | Spector | 128/203.28 |
| 4,374,521 A | 2/1983 | Nelson et al. | |
| 4,539,985 A | * 9/1985 | Magrath | 128/205.13 |
| 4,589,684 A | * 5/1986 | Nowacki et al. | 285/319 |
| 4,633,890 A | * 1/1987 | Carden | 128/202.27 |
| 4,641,646 A | * 2/1987 | Schultz et al. | 128/207.14 |
| 4,774,941 A | 10/1988 | Cook | |
| 4,790,327 A | * 12/1988 | Despotis | 128/207.14 |
| 4,856,548 A | 8/1989 | Paluch | |
| 4,919,132 A | 4/1990 | Miser | |
| 5,163,424 A | 11/1992 | Køhnke | |
| 5,359,998 A | 11/1994 | Lloyd | |
| 5,485,835 A | 1/1996 | Vande Streek et al. | |
| 5,520,173 A | 5/1996 | Kuhn | |
| 6,098,621 A | * 8/2000 | Esnouf | 128/205.13 |

FOREIGN PATENT DOCUMENTS

| | | |
|---|---|---|
| AU | A 33029/78 | 8/1979 |
| DE | 1 784 600 | 8/1971 |
| DE | 24 24 798 A1 | 11/1975 |
| EP | 0 367 285 A2 | 5/1990 |
| FR | 2 326 943 | 5/1977 |
| FR | 2 614 207 | 10/1988 |
| FR | 2 696 350 A1 | 4/1994 |
| GB | 550725 | 1/1943 |
| GB | 2 139 099 A | 11/1984 |
| WO | WO 84/01295 | 4/1984 |

* cited by examiner

Primary Examiner—Aaron J. Lewis
Assistant Examiner—Joseph F. Weiss, Jr.
(74) Attorney, Agent, or Firm—Seed IP Law Group PLLC

(57) ABSTRACT

A disposable oxygenating device (2) comprising a body (4,40) and a collapsible bag (16) coupled thereto, the body including first coupling means (6) being couplable to a source of oxygen, second coupling means (10) being couplable to an endotracheal tube, laryngeal mask or the like, a connector (14) to which the bag (16) is connected, an oxygen duct (7) in fluid communication with the first coupling means having an outlet orifice (22) which in use delivers oxygen from the source of oxygen to inflate the bag with oxygen, and an outlet (20,44), the arrangement being such that, in use, during an inspiration cycle, oxygen from the bag passes through the second coupling means (10) and, during an expiration cycle, expiration products pass through the body (2,40) and are expelled through the outlet (20,44).

10 Claims, 4 Drawing Sheets

DISPOSABLE OXYGENATING DEVICE

CROSS-REFERENCE TO RELATED APPLICATION

This application is a continuation of pending U.S. patent application Ser. No. 09/043,234, filed Sep. 25, 1998, now U.S. Pat. No. 6,098,621 which is a conversion of International Application No. PCT/AU96/00417, which, in turn, claims priority from Australian Application No. PN 5384 filed Sep. 12, 1995.

This invention relates to a disposable oxygenating device.

In the post operative treatment of patients, it is usually desirable to supply oxygen or oxygen enriched air to a patient for a period of say 5 to 15 minutes to assist in reoxygenating the patient to offset the effects of the anesthetic. Usually oxygen is available in recovery rooms from suppliers which are capable of delivering oxygen at a rate of about 4 to 6 liters per minute. Unfortunately this is less than the rate of inspiration of a typical adult patient. Some attempts have been made to provide an oxygen storage device which can store oxygen from a relatively low capacity supply so as to be able to deliver the oxygen or oxygen enriched air to the patient at a relatively high rate during inspiration.

SUMMARY OF THE INVENTION

An object of the present invention is to provide a disposable oxygenating device which is capable of delivering oxygen or oxygen rich air to a patient at relatively high flow rates.

According to the present invention there is provided a disposable oxygenating device comprising a body and a collapsible bag coupled thereto, the body including at least first, second and third openings, the first opening being couplable to a source of oxygen, the second opening being couplable to an endotracheal tube or a laryngeal mask or the like, and the third opening being in fluid communication with the interior of the bag. The arrangement is such that in use oxygen enters the body through the first opening and fills the bag so that during the inspiration cycle of the patient, oxygen stored in the bag can be rapidly delivered through the second opening to the endotracheal tube or the laryngeal mask The invention also provides a disposable oxygenating device comprising a body and a collapsible bag coupled thereto, the body including first coupling means being couplable to a source of oxygen, second coupling means being couplable to an endotracheal tube, laryngeal mask or the like, a connector to which the bag is connected, an oxygen duct in fluid communication with the first coupling means having an outlet orifice which in use delivers oxygen from the source of oxygen to inflate the bag with oxygen, and an outlet, the arrangement being such that, in use, during an inspiration cycle, oxygen from the bag passes through the second coupling means and, during an expiration cycle, expiration products pass through the body and are expelled through said outlet.

BRIEF DESCRIPTION OF THE DRAWINGS

The invention also provides a method of oxygenating a patient having an endotracheal tube or laryngeal mask applied to him or her using a disposable oxygenating device having an inflatable bag comprising coupling the device to the endotracheal tube or laryngeal mask continuously supplying oxygen to the bag thereby inflating the bag with oxygen, permitting the bag to collapse during an inspiration cycle of the patient whereby oxygen from the bag is delivered to the patient through the endotracheal tube or laryngeal mask, and providing an outlet in the device whereby during an expiration cycle products of expiration are permitted to escape the device.

It is preferred that the bag is formed from a film of plastics material. Preferably the material comprises high density polyethylene.

Preferably the film is about 15 microns in thickness.

The bag may have a vent hole near an end thereof remote from the body.

Preferably the bag has a capacity in the range 250 to 500 ml.

Preferably the body has fourth openings therein for allowing air to be entrained into the stream of oxygen entering the body through the first opening so as to dilute the concentration of oxygen in the bag. Preferably the concentration of oxygen in the bag is in the range from 40% to 60% and the number and size of the fourth openings can be adjusted accordingly to achieve this concentration.

Preferably further, the body is injection moulded from plastics material and the bag is adhered, bonded or welded thereto.

It will be appreciated that the device can be constructed of low cost materials so that it is cheap enough for disposal after a single use. This thereby avoids the need for sterilisation and/or autoclaving.

Figure 1:
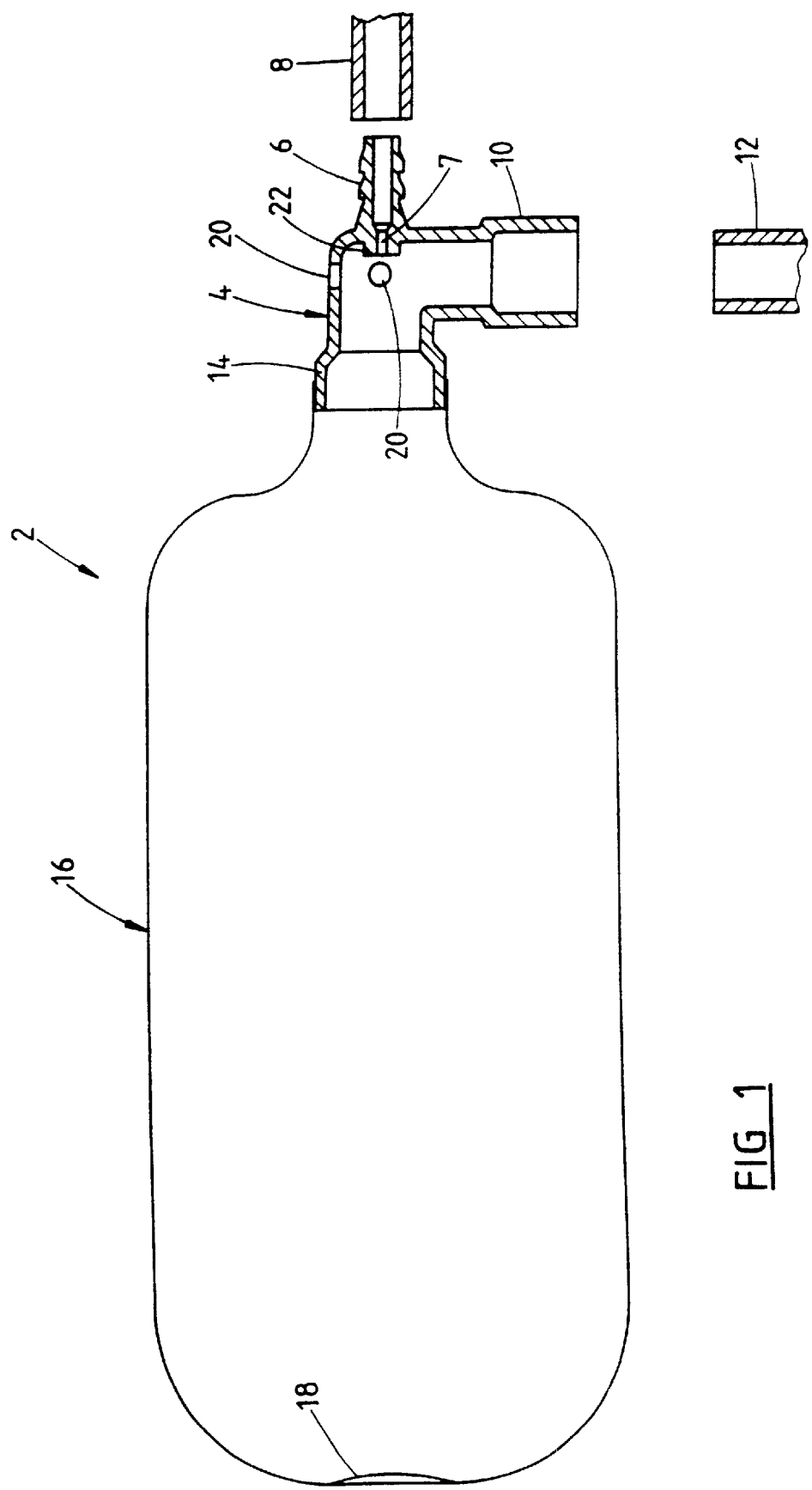
Figure 2:
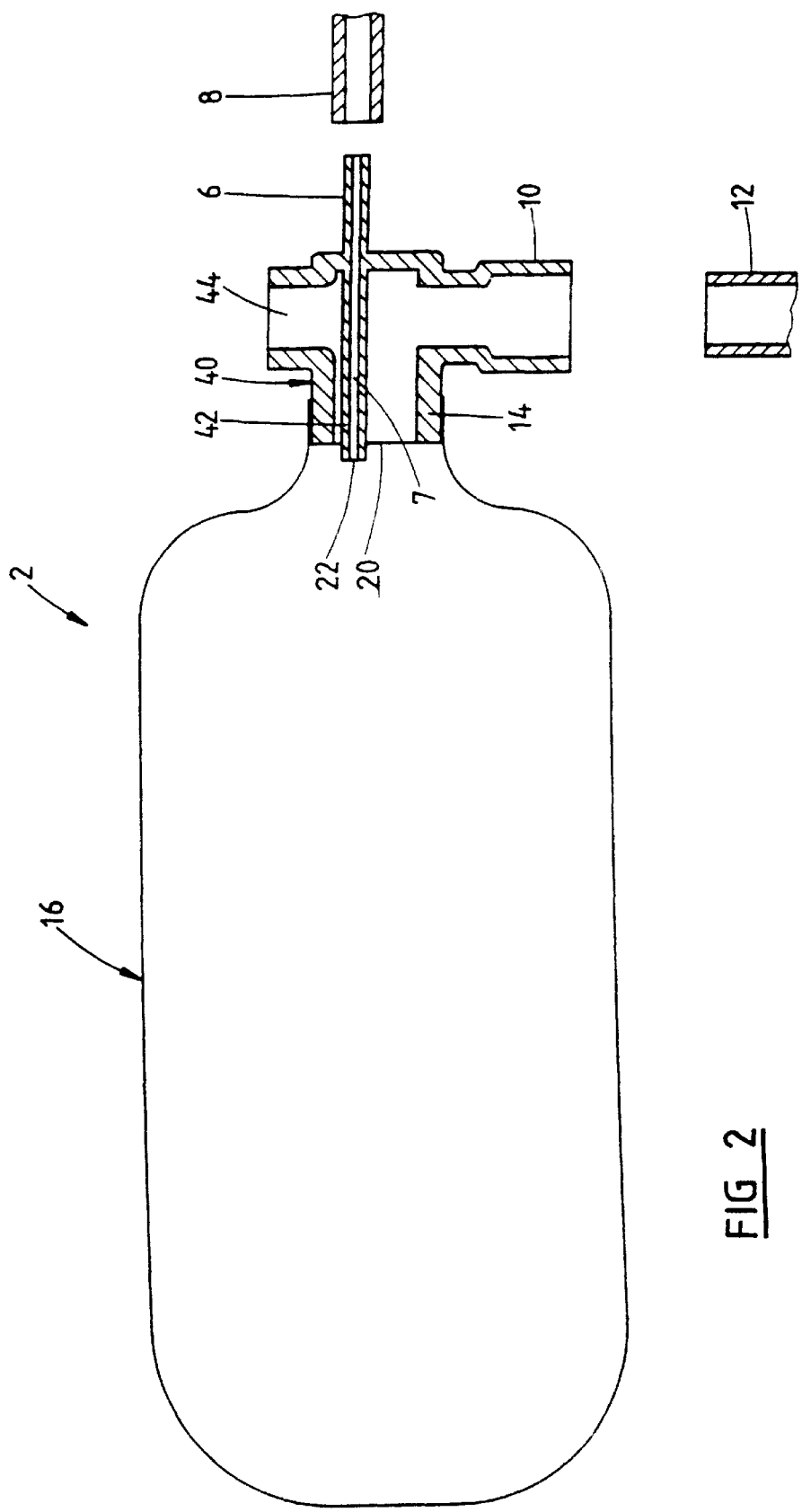
Figure 3:
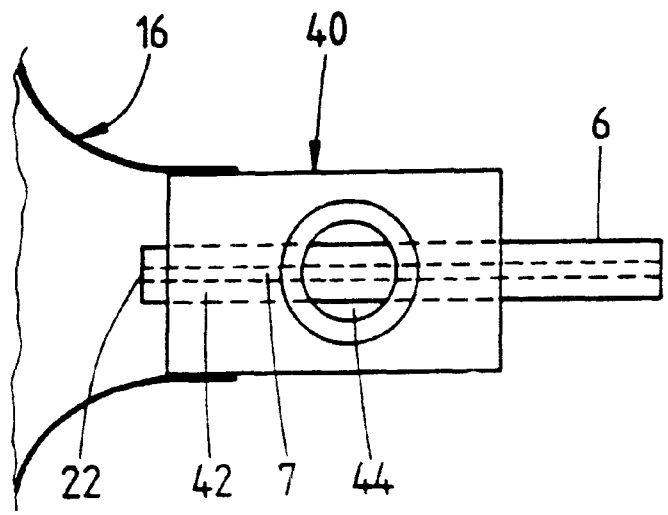
Figure 4:
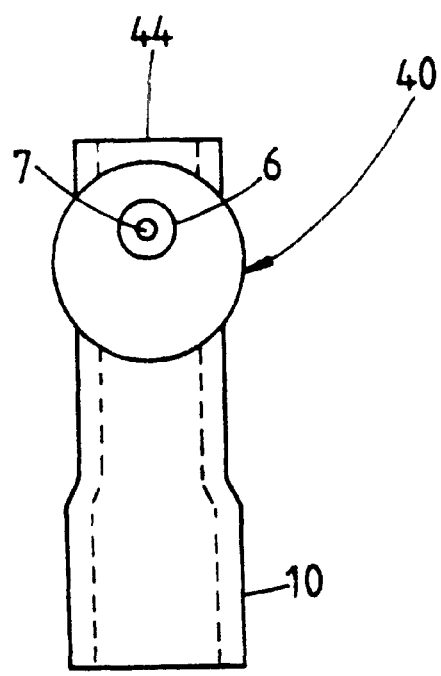

The invention will now be further described with reference to the accompanying drawings, in which:

FIG. 1 is a schematic view of a first embodiment of a disposable oxygenating device constructed in accordance with the invention;

FIG. 2 is a schematic view of a second embodiment of a disposable oxygenating device constructed in accordance with the invention;

FIG. 3 is a plan view of the elbow shown in FIG. 2;

FIG. 4 is an end view of the elbow shown in FIG. 2; and

Figure 5:
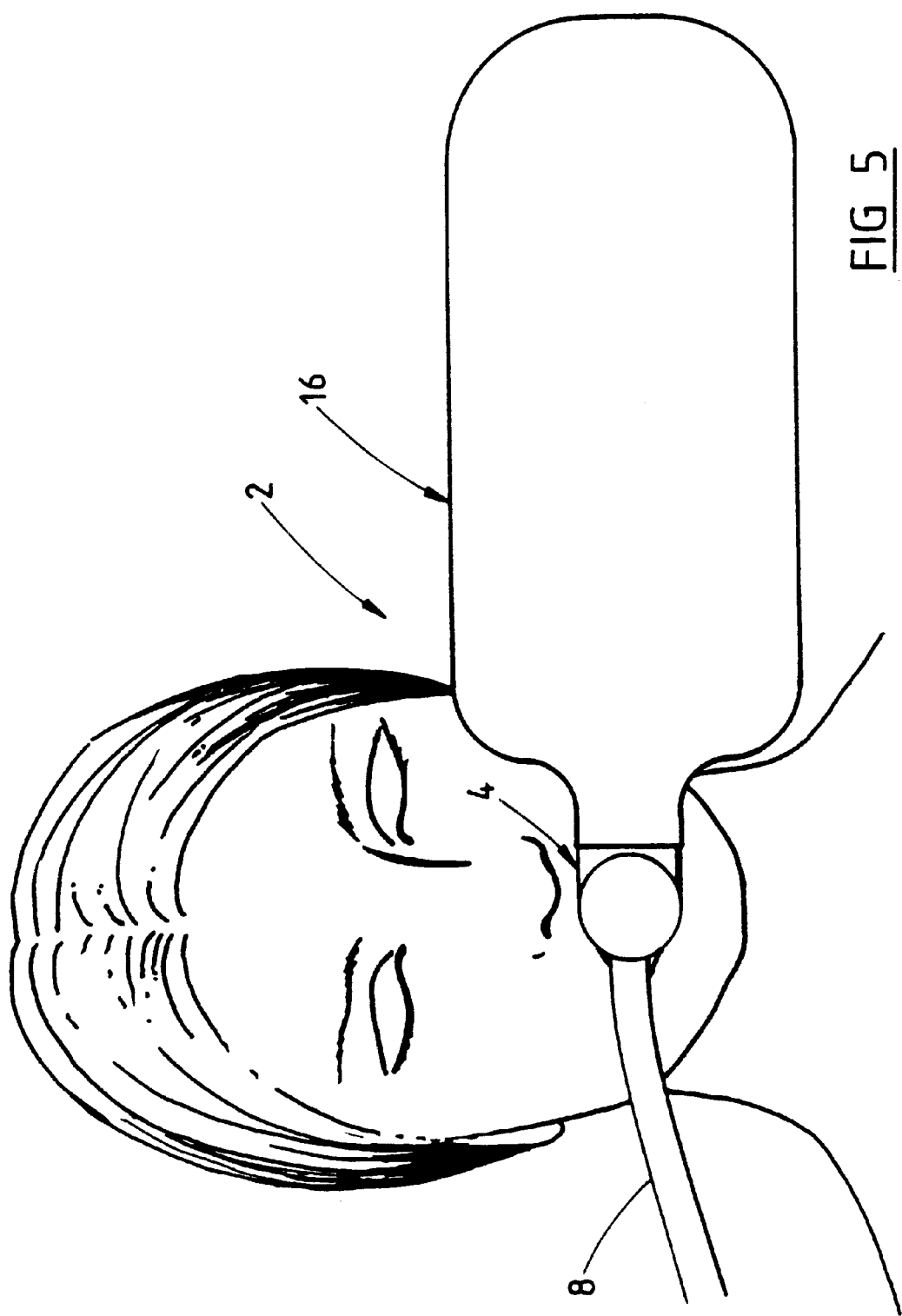

FIG. 5 schematically illustrates the manner in which the device is used.

DETAILED DESCRIPTION OF THE DRAWINGS

The disposable oxygenating device 2 shown in FIG. 1 comprises an elbow 4 and a collapsible bag 16. The elbow 4 is preferably injection moulded from plastics material such as high density polyethylene. It generally comprises a hollow body having a barbed inlet spigot 6 having an oxygen supply duct 7. The spigot 6 can be inserted in an oxygen supply tube 8 which is connected to a supply of compressed oxygen (not shown). The elbow 4 includes a tapered socket 10 which can be coupled to a male coupling 12 which is formed on the end of an endotracheal tube (oral or nasal) or laryngeal mask (not shown). The socket 10 has an internal bore which is compatible with complementary fittings on endotracheal tubes or laryngeal masks. Preferably the bore is 15 mm. The elbow 4 further includes a coupling connector or SP which is connected a collapsible bag 16. The bag 16 includes a vent opening 18 located remote from the elbow 4.

In the preferred form of the invention, the collapsible bag 16 is formed from high density polyethylene film having a thickness in the range from 5 to 15 microns and preferably 15 microns in thickness. The volume of the bag is in the range from 250 to 500 ml. Preferably the length is about 170 mm and the diameter about 80 mm. The vent hole preferably has a circular opening approximately 1 cm in diameter. The bag 16 may be formed from a continuous tube of plastics material which is heat welded so as to have closed ends, one of which is heat welded or adhered to the spigot 14 and the other forms the end in which the opening 18 is located.

The elbow 4 also includes a number of air inlet openings 20 which are located adjacent to an inlet orifice 22 of the spigot 6. The arrangement is such that when oxygen passes from the inlet orifice 22 and the arrangement is such that the constricted size of the inlet orifice 22 causes a relatively high velocity of oxygen flowing into the bag 16 whereby oxygen is drawn into the elbow 4 through the openings 20. This dilutes the oxygen in the bag 16 to a preferred concentration preferably in the range 40% to 60%. The actual concentration will depend upon a number of parameters including the inlet pressure of the oxygen, the diameter of the inlet orifice 22 and the number and size of the openings 20. In the preferred embodiment, the orifice 22 has a bore of approximately 1.5 mm and there are three of the openings 20 each having a diameter of about 5 mm.

The openings 20 also have an important safety factor in circumstances where the source of oxygen connected to the tube 8 fails. If the openings 20 were not present, expired air would be collected in the bag 16 which could cause asphyxiation of the patient. With the openings 20 being present however, the patient will draw fresh air through the openings 20 so as to avoid this problem.

The disposable oxygenating device of the invention is particularly useful for oxygenating patients who are recovering from general anaesthesia which has been administered by a laryngeal mask or an endotracheal tube. The laryngeal mask or endotracheal tube are left in the patient and the socket 10 of the device is coupled to the coupling 12 of the mask or tube. An oxygen supply tube 8 which is coupled to a source of oxygen normally limited to a flow rate of about 4 to 6 liters a minute is connected to the inlet spigot 6. Oxygen passes through the inlet orifice 22 and may draw some air into the elbow 4 through the openings 20 so that the bag 16 is filled with oxygen enriched air. When the patient inspires, the oxygen rich air passes from the bag 16 through the socket 10 into the laryngeal mask or endotracheal tube. It will be noted that the internal passage from the coupling spigot 14 to the socket 10 is relatively wide and unconstricted so as to provide for good fluid flow therethrough. With the device of the invention, the rate of delivery of oxygen rich air can be optimum, say at about 20 liters per minute, which is normally much greater than that available in many recovery rooms.

When the patient expires, the bag 16 will be expired with expiratory gases. The expiratory gases will, however, be flushed out from the bag 16 through the opening 18 by new oxygen enriched air entering the elbow 4 from the spigot 6 and openings 20.

FIGS. 2, 3 and 4 illustrate a preferred embodiment of the invention. In these drawings the same reference numerals have been used to denote parts which correspond to one another where appropriate. The main difference between the device shown in FIG. 2 and that shown in FIG. 1, is that the bag 16 does not include the vent opening 18. Further, the outlet orifice 22 is located at the end of a conduit 42 which extends through the coupling spigot 14 so that oxygen passes directly into the interior of the bag 16. In this embodiment, the elbow 40 does not include a plurality of openings 20 but rather has a single relatively large opening 44 which is generally oppositely disposed to the socket 10, as seen in FIG. 2.

The elbow 40 may be injection moulded from suitable plastics material such as high density polyethylene. Moulding could be facilitated if the conduit 42 were not separately formed so as to extend through the coupling. In this case the oxygen passage 7 from the inlet spigot 6 could be moulded into the side wall of the elbow and it would still function correctly provided that the outlet orifice 22 opens into the interior of the bag 16 or is located close to the interior of the bag 16. The bag 16 maybe heat seamer and trimmed into the shape of a bag. Its neck could be heat seamed onto the coupling spigot 14. The inlet spigot 6 need not be formed with barbs as shown in FIG. 1 but may be smooth or provided with small serrations (not shown). The oxygen passage 7 through the opening 16 leading to the orifice 22 is preferably about 1.5 mm in diameter. The spigot 6 itself may have a 4 mm outer diameter. The socket 10 is preferably formed as a 15 mm tapered fitting for receipt of the end of an endotracheal tube, laryngeal mask or other device. The opening 44 preferably has a diameter of about 10 mm. The bag 16 preferably has a length of about 170 mm and a flattened width of about 80 mm thereby providing a volume of about 250 ml when inflated.

In use of the device shown in FIGS. 2 to 4, the bag 16 is inflated with oxygen from the supply tube 8 through the orifice 22. The supply tube 8 delivers the oxygen at a nominal rate of say 6 liters per minute. During the inspiration cycle of the patient, oxygen collected in the bag 16 is delivered through the socket 10 to the tube 12. This preferably provides a volume of about 250 mm of oxygen.

The bag 16 refills with oxygen from the oxygen supply tube 8 during the pause between the end of inspiration and commencement of expiration. The expiratory air tends to pass dry from the socket 10 through the opening 44. This prevents significant dilution of the oxygen in the bag 16 by the expiratory fluid passing into the elbow 40 from the tube 12. Experiments have shown that the device shown in FIGS. 2 to 4 performs better than that shown in FIG. 1 because in the embodiment of FIGS. 2, 3 and 4, more undiluted oxygen is available from the bag 16 to the patient than is in the case of the embodiment of FIG. 1.

FIG. 5 shows the preferred manner in which the device 2 is used. It will be seen that the bag 16 is located generally transversely to a reclining patient and the tube 8 extends on the opposite side of the patient. The endotracheal tube or laryngeal mask passes through the mouth of the patient in the usual way. In operation the bag 16 will collapse (or partly collapse) which provides a visual indication to recovery room staff that the patient is breathing.

It will be appreciated by those skilled in the art that the device of the invention can be made from inexpensive materials and is therefore cheap enough to be disposable. It does not need any valves which, if needed, could make manufacture more expensive and possibly compromise the reliability of the device.

As indicated above, the device can be used with oral or nasal endotracheal tubes or laryngeal masks. It is quite possible that the same device can be used in other applications such as for coupling to a tracheotomy tube.

Many modifications will be apparent to those skilled in the art without departing from the spirit and scope of the invention.

What is claimed is:

1. A disposable oxygenating device for passively providing oxygenat to a breathing patient after administration of an anesthetic, the device comprising a body and a collapsible bag having non-recoiling side walls coupled thereto, the body consisting of an integral moulding from plastic material and has first coupling means being couplable to a source of oxygen, second coupling means being couplable to an endotracheal tube or laryngeal mask, a connector to which the bag is connected, an oxygen duct in fluid communication with the first coupling means having an orifice which in use delivers oxygen from the source of oxygen to inflate the bag with oxygen, the bag being of a plastic film sufficiently thin and pliable to collapse as a result of the inspiration cycle of the patient, and an outlet, the arrangement being such that, in use, during an inspiration cycle, oxygen from the bag passes through the second coupling means and, during an expiration cycle, expiration products pass through the body and are expelled through said outlet.

2. A device as claimed in claim 1 wherein the body and bag are formed from the same material whereby the bag can be heat or ultrasonically welded to the connector.

3. A disposable oxygenating device for passively providing oxygenat to a breathing patient after administration of an anesthetic, the device comprising a body and collapsible bag having non-recoiling side walls coupled thereto, the body including first coupling means being couplable to a source of oxygen, second coupling means being couplable to an endotracheal tube or laryngeal mask, a connector to which the bag is connected, an oxygen duct in fluid communication with the first coupling means having an orifice which in use delivers oxygen from the source of oxygen to inflate the bag with oxygen, and an outlet, the arrangement being such that, in use, during a natural inspiration cycle, oxygen from the bag passes through the second coupling means and, during an expiration cycle, expiration products pass through the body and are expelled through said outlet, the bag being a high density polyethylene film that is sufficiently thin and pliable to collapse as a result of the natural inspiration of the patient.

4. A device as claimed in claim 3 wherein said sheet plastic material has a thickness in the range of about 5 to 15 microns.

5. A device as claimed in claim 4 wherein the bag has a volume of about 250 ml when inflated.

6. A disposable oxygenating device for passively providing oxygen to a breathing patient, the device comprising a body and a collapsible bag having non-recoiling side walls coupled thereto, the body including first coupling means being couplable to a source of oxygen, second coupling means being couplable to an endotracheal tube or laryngeal mask, a connecting spigot having an open end, an oxygen duct in fluid communication with the first coupling means having an orifice which in use delivers oxygen from the source of oxygen to inflate the bag with oxygen, and an outlet located adjacent to the open end of the spigot, and wherein the bag is connected to the spigot, the bag being of a plastic film sufficiently thin and pliable to collapse as a result of the natural inspiration of the patient, the arrangement being such that, in use, during a natural inspiration cycle, oxygen from the bag passes through the second coupling means and, during an expiration cycle, expiration products pass through the body and are expelled through said outlet without filling the bag.

7. A disposable oxygenating device for passively providing oxygenat to a breathing patient after administration of an anesthetic, the device comprising a body and a collapsible bag having non-recoiling side walls coupled thereto, the body including first coupling means being couplable to a source of oxygen, a socket being couplable to an endotracheal tube or laryngeal mask, a connector to which the bag is connected, an oxygen duct in fluid communication with the first coupling means having an orifice which in use delivers oxygen from the source of oxygen to inflate the bag with oxygen, the bag being of a plastic film sufficiently pliable to collapse as a result of the inspiration cycle of the patient, and an outlet which is generally aligned with the socket, the arrangement being such that, in use, during an inspiration cycle, oxygen from the bag passes through the socket and, during an expiration cycle, expiration products pass through the body in a substantially linear flow path and are expelled through said outlet without filling the bag.

8. A method of passively providing supplemental oxygen to a breathing patient after administration of anesthetic, the method comprising:

providing the patient with an endotracheal tube or laryngeal mask;

coupling to the tube or mask a disposable oxygenating device having an inflatable bag of plastic film that is sufficiently thin and pliable to collapse as a result of the patient's inspiration cycle;

coupling a continuous supply of oxygen to the bag to inflate the bag with the oxygen without expansion of the surface area of the sheet plastic material;

permitting the bag to collapse during the inspiration cycle of the patient whereby oxygen from the bag is automatically delivered to the patient through the endotracheal tube or laryngeal mask without the necessity of manually deforming the bag;

delivering oxygen to the bag during a pause between the end of the inspiration cycle and the beginning of an expiration cycle; and providing an outlet in the device whereby during the expiration cycle products of expiration escape the device without filling the bag.

9. A method as claimed in claim 8 wherein the volume of the bag is such that oxygen therefrom is delivered to the patient at a rate which is greater than that available from the oxygen supply which supplies oxygen to the bag.

10. A method as claimed in claim 8 wherein oxygen is supplied to the bag through an orifice which is adjacent to the bag, and the outlet is generally aligned with the endotracheal tube or laryngeal mask whereby products of expiration tend to pass through the device without entering the bag.

* * * * *

UNITED STATES PATENT AND TRADEMARK OFFICE
CERTIFICATE OF CORRECTION

PATENT NO. : 6,508,250 B1
DATED : January 21, 2003
INVENTOR(S) : Philip Stuart Esnouf It is certified that error appears in the above-identified patent and that said Letters Patent is hereby corrected as shown below:

<u>Title page,</u>
Item [63], Related U.S. Application Data, "filed as application No. PCT/AU96/00417 on Sep. 12, 1995" should read as -- filed as application No. PCT/AU96/00417 on Jul. 2, 1996 --

Signed and Sealed this

Fifth Day of April, 2005

JON W. DUDAS
*Director of the United States Patent and Trademark Office*